United States Patent [19]

Zerhouni et al.

[11] Patent Number: 5,196,343

[45] Date of Patent: Mar. 23, 1993

[54] ULTRASONIC CALIBRATION MATERIAL AND METHOD

[76] Inventors: Moustafa B. Zerhouni; Mohammed Rachedine, both of Computerized Imaging Reference Systems, Inc. 2428 Almeda Ave., Suite 212, Norfolk, Va. 23513

[21] Appl. No.: 592,678

[22] Filed: Oct. 4, 1990

[51] Int. Cl.$^5$ .................... G01N 29/00; G01N 31/00; G01N 33/483; G21F 1/10
[52] U.S. Cl. .......................... 436/8; 73/644; 252/315.2; 252/408.1; 523/137
[58] Field of Search ............ 252/315.2, 408.1; 428/402.24, 317.9; 73/644; 523/137; 524/437; 436/8

[56] References Cited

U.S. PATENT DOCUMENTS

| | | | |
|---|---|---|---|
| 3,663,842 | 5/1972 | Miller | 73/644 X |
| 4,002,221 | 1/1977 | Buchalter | 73/644 X |
| 4,021,364 | 5/1977 | Speiser et al. | 428/402.24 |
| 4,277,367 | 7/1981 | Madsen et al. | 252/408.1 |
| 4,365,516 | 12/1982 | Molina | 73/644 |
| 4,523,122 | 6/1985 | Tone et al. | 73/644 X |
| 4,674,512 | 6/1987 | Rolf | 128/640 |
| 4,813,402 | 3/1989 | Reichenberger et al. | 73/644 X |
| 4,895,574 | 1/1990 | Rosenberg | 623/14 |
| 4,905,700 | 3/1990 | Wokalek et al. | 73/644 X |
| 4,906,421 | 3/1990 | Plamthottam et al. | 264/171 X |
| 4,940,740 | 7/1990 | Folda et al. | 523/428 |
| 5,053,341 | 10/1991 | Companion | 436/8 |

FOREIGN PATENT DOCUMENTS

| | | | |
|---|---|---|---|
| 0153296 | 8/1985 | Japan | 73/644 |
| 0728079 | 4/1980 | U.S.S.R. | 73/644 |

*Primary Examiner*—Richard D. Lovering

[57] ABSTRACT

Ultrasonic calibration material produced by polymerization of acrylamide with N,N'-methylene-bis-acrylamide in vacuum-degassed liquid solutions such as water, ethylene glycol, emulsions of non-miscible liquids with water and blends of liquids in which a homogeneous and permanent suspension of solid and liquid particles (e.g.: alumina, boron nitride, graphite, water-filled phenolic microspheres, glass microspheres, polyethylene, turpentine oil) is chemically achieved by polymerization of an acrylic acid polymer.

9 Claims, 14 Drawing Sheets

ULTRASONIC CALIBRATION MATERIAL AND METHOD

FIELD OF INVENTION

This invention relates to an ultrasonic calibration material for use in ultrasound calibration devices designed for testing and calibrating medical ultrasound equipment, or for adjusting the ultrasound beam between a transducer and the scanned object, or for training personnel in the use of ultrasound equipment.

DESCRIPTION OF PRIOR ART

Heretofore, ultrasonic calibration materials generally available have been liquid/oil mixtures or gels.

Work on this invention was started in response to a number of commercial inquiries from customers searching for ultrasound tissue-mimicking material which did not have the limitations of existing commercial materials and where the inadequacy of existing materials were specifically stated. Existing materials (generally described in U.S. Pat. No. 4,277,367) are described as congealed matrixes which required periodic factory-based replenishment of moisture following desiccation of the matrix and as having a general limitation against multi-tissue simulation in the same simulation test envelope.

Our new material exhibits an excellent simulation of the ultrasonic characteristics of human soft tissues, either individually or in combination. The formulation of this new material can be precisely adjusted to cover the range of acoustic speed and attenuation displayed by human soft tissues and, when imaged by diagnostic ultrasonic imagers, it displays the same texture patterns as displayed by human soft tissues, thus indicating the same scattering properties.

Most of the existing materials used in the medical ultrasound imaging field for tissue simulation, for testing, or for training devices consist of a background of a thermally reversible congealed matrix of pudding-like consistency in which solid or liquid additive particles have been homogeneously suspended by the use of a mechanically driven rotating device designed to counteract the natural segregation of said particles during the congelation process of the matrix.

A congealed gel based matrix will reverse to a liquid state when subjected purposefully (such as in an experiment), or accidentally to temperatures above 78 degrees Celsius. This temperature related change results in a melted gel with different sonic properties from those demonstrated in the gel state. Additionally, such a reversion would allow natural segregation of the added particles to take place and will permanently change the sonic properties of the material when the gel material returns back to a normal room temperature. Our invention addresses this point directly.

To produce a congealed gel material, the initial components used to fabricate a congealed gel based matrix need to be heated above the melting temperature of the gel and this precludes or renders difficult the use of temperature sensitive components such as wax or liquids of low volatility.

One of the most challenging difficulties in simulating soft tissues is in the production of a material which is able to retain a high water content (from 50 up to 95% by weight) having physical characteristics resembling flesh consistency and further able to sustain normal usage and handling.

Thermally reversible congealed gel based matrix, like alimentary gel have a very low resistance to physical stress, and without an adequately designed and engineered protective envelope they cannot be used with ultrasonic instrumentation. Such fragility does not allow the normal use of said material in direct contact with the ultrasonic instrumentation. On the other hand, the protective envelope in itself is a hinderance in the ultrasonic use of the material because of its possible adverse interference with the ultrasonic beam.

Desiccation is the most common concern for all ultrasonic simulating materials due to the high content of water necessary to properly simulate soft tissues.

Up to now, the engineered solutions to the desiccation problem have not been successful in providing a satisfactory response to limit the rate of desiccation, or after desiccation, to provide an easy alternative for replenishment. For a device made of thermally reversible congealed gel based matrix, it is necessary to return the device containing said matrix to the original fabricator in order for the device to be properly overhauled.

Up to now, materials with a water based gel-matrix, made from animal or vegetable gelatin have been extensively used because they display sonic characteristics which are in the same range as those found when imaging human tissues.

Fine tune adjustments of the sonic properties of the new materials are obtained by adding liquids which are miscible with water, and/or adding solid particles, and/or adding liquid particles after emulsification of a non-miscible liquid with water.

The adequacy of a background matrix for its use in the development of ultrasound test/calibration materials can be judged from:

a) the intrinsic ultrasound properties of such a background matrix which experience has shown should be that of human liver. Thus, the gray scale echo appearance of the material should be similar to the gray scale echo appearance of human liver. Also, the acoustic attenuation of the test material should be approximately proportional to the ultrasonic frequency being used and again should be similar to the imaging properties of human soft tissues. If we assume that the acoustic attenuation A is a power function of the sonic frequency F as follows:

$$A = A_0 F^n$$

then the test material should exhibit values of the power coefficient n close to one. Values in the range of 0.8 to 1.2 indicate a good proportionality of the acoustic attenuation with the sonic frequency.

b) the extent of the compatibility of such a matrix to various solid and liquid additives.

c) the physical properties of such a matrix which govern its physical integrity under expected usages and handling.

d) the ease in the fabrication and reproducible uniformity.

e) the ease of preservation of the material in its original condition over time.

The most commonly referred-to ultrasonic simulating materials are materials based on thermally reversible congealed gel matrix formed with animal or vegetable gelatin. Their main disadvantages are their sensitivity to heat due to their low melting point and their fragility under normal usages and handling.

OBJECTS AND ADVANTAGES

Accordingly, a new approach to ultrasonic calibration material is needed.

It is an object of this invention to produce and to provide a method for producing an ultrasonic calibration material with speed of sound in the range of 1420 m/s up to 1650 m/s and with acoustic attenuation in the range of 0.1 to 1.50 Db/cm/MHZ in the frequency range of 2 to 10 MHz.

Further, it is the object of this invention to produce ultrasonic calibration material which can be easily refreshed and preserved by the user, and which can simulate multi-tissue sequences.

It is another object of this invention to provide a new material which displays a gray scale echo appearance identical to human liver tissue which indicates similar back-scattering characteristics, when scanned by ultrasound imaging equipments.

It is another object of this invention to provide a material of the character described wherein the background matrix can accept an extended range of solid additive particles such as alumina, boron nitride, phenolic microspheres, polyethylene powder, graphite, glass microspheres as well as liquid additives such as ethylene glycol, alcohols, turpentine oil, vegetable or organic oils.

It is another object of this invention to provide a material which can be manufactured at room temperature and of the character described wherein the background matrix can accept additives of low melting temperature.

It is another object of this invention to provide a material of the character described wherein its compatibility to additives provides flexibility and a wide range of choice in additives for the purpose of adjusting the sonic properties of the material as desired.

It is another object of this invention to provide a material of the character described which is able to contain up to 95% water by weight and its physical properties are such that it can withstand much higher physical stress than a congealed matrix can withstand and temperature up to 100 degrees Celsius.

It is another object of this invention to provide a material which can be normally handled and used with or without a protective envelope.

It is a still further object of this invention to provide a material of the character described wherein this new material is a SOLID ELASTIC with a hard-boiled egg consistency.

It is another object of the present invention to provide a material of the character described wherein the background matrix is, by itself, immune from bacterial attack.

It is another object of the present invention to provide a material of the character described wherein the background matrix of this new ultrasound material is formed through polymerization of acrylamide with N,N'-methylenebis-acrylamide (MBA) in liquids. The process of polymerization is initiated in the present invention by N,N,N', N'-tetra-methyl-ethylene-diamine (TEMED) which is itself activated by ammonium persulfate (AP). The polymerization can be achieved in different liquids and we experience by way of illustration and not by way of limitation, complete polymerization in pure water as well as in pure ethylene glycol.

It is still another object of the present invention to provide a material of the character described wherein the polymerization can be easily controlled by adjusting the amount of initiator (TEMED) and activator (AP) to the point that it is possible to achieve the polymerization in less than two minutes.

In water, depending on the amount of acrylamide used in the present invention, we can produce a soft self-standing solid elastic with 5% by weight acrylamide up to a very firm solid elastic with 18% acrylamide. Such materials retain the shape and dimensions of the mold in which they have been poured before polymerization.

With ethylene glycol we produced a tacky and very comfortable soft solid elastic with 10 up to 20% acrylamide by weight. The elastic matrix produced from ethylene glycol (only) displays speed of sound above 1700 m/s and acoustic attenuation below 0.15 Db/cm/MHz. Because of the very low volatility of the ethylene glycol such matrixes are practically immune from desiccation.

Prior methods of manufacturing of materials based on thermally reversible congealed gelatin requires that the gel solution be at a temperature above the melting point of the gel prior to pouring into a mold for cooling and in turn gelification. It is very difficult to produce multi-layered materials of different acoustic characteristics based on a congealed matrix because of the basic requirements of pouring a molten hot, ungelified solution against an already cold congealed matrix—which itself is then partially melted and disturbed by the pouring process.

Polymerized resin matrixes are molded at room temperature and they are insensitive to temperature up to 100 degrees Celsius. Thus, it is an easy task to produce a multi-layered material or even to embed a piece of material of any size and shape with particular sonic properties within another material with different sonic properties. By using such a process in the present invention, we provide the ability to easily simulate different soft-tissue configurations within the same device. 1

BRIEF DESCRIPTION OF DRAWINGS

Other objects and advantages of this invention appear hereinafter and for the purposes—but not of limitations—reference is made to the following drawings in which.

DRAWING REFERENCE NUMERALS

Figure 1:
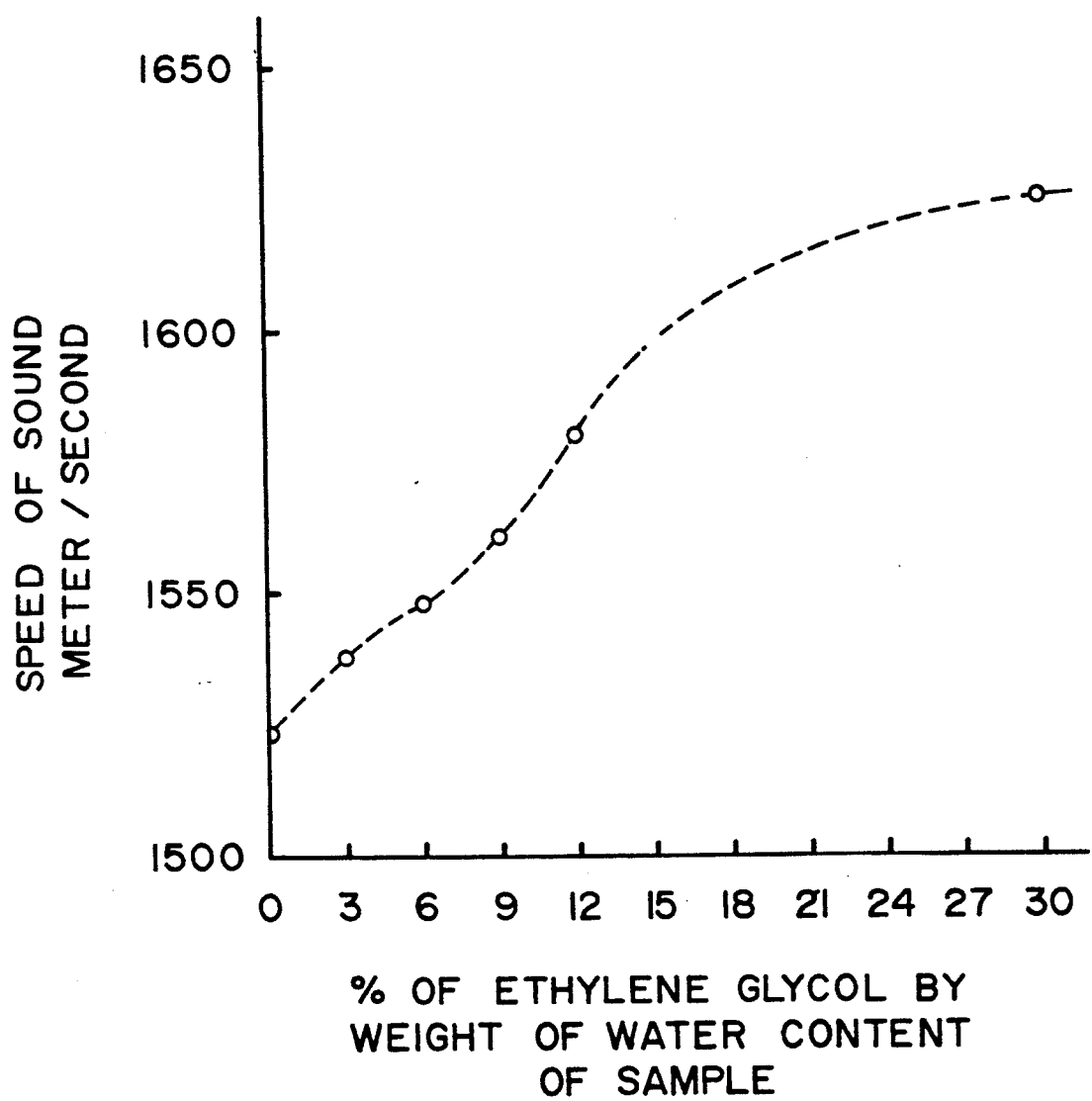
FIG. 1 is a chart showing speed of sound as a function of ethylene glycol content in sample.

1. Sample of ultrasonic calibration material
1b. Sample of ultrasonic calibration material contained in (30)
2. Water
3. Container
4. Acrylic Acid Polymer
5. Methyl-p-Hydroxybenzoate
6. Acrylamide
7. N,N'-Methylene-bis-Acrylamide
8. Ethylene-Glycol
9. Solution containing (2), (4), (5), (6), (7), and (8)
9a. Solution containing (2), (4), (5), (6), and (7)
10. Cup with solution (9)
10a. Cup with solution (9a)
11. Alumina
12. Solution in (31)
13. Solution in (32)
14. Solution in cup (10) containing (9), (12), and (13)
14a. Solution in cup (10a) containing (9a), (26), (34), (12), and (13)
15. Vacuum Chamber
16. Solution in (33)
17. Solution in cup (10) containing (14) and (16)
17a. Solution in cup (10a) containing (14a) and (16)
18. Mold
19. Bottom of (18)
20. Top flat glass of (18)
21. Ultrasound reflective glass
22. Single crystal transducer
23. Ultrasonic, narrow band transducer
24. Oscilloscope
25. Water
26. Turpentine Oil
28. Top surface of sample (1b)
29. Nylon monofilaments
30. Poly(methyl)methacrylate (PMMA)
31. Syringe A
32. Syringe B
33. Syringe C
34. Surfactant
35. N,N,N1N1-Tetra-Methyl-Ethylene-Diamine
36. Sodium Hydroxide
37. Ammonium Persulfate
38. Membrane
50. Sifter

DESCRIPTION

As described above, the present invention comprises a novel ultrasonic test material, generally designated (1) in the drawings, and a method of producing same.

We have produced ultrasonic calibration material in which the suspending agent is a neutralized acrylic acid polymer having the following general chemical structure:

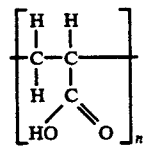

We have found, in development of this invention, that the speed of sound in such new materials can be adjusted in the range of 1420 up to 1650 m/s and that the acoustic attenuation can be adjusted between 0.1 to 1.5 Db/cm/MHz up to 8 MHz while maintaining proportionality of the acoustic attenuation with the ultrasonic frequency by using different particles as dampening additives in the background matrix.

Measurements made on samples of the basic polyacrylamide-in-water solid elastic matrix with no additives indicate a speed of sound in the range of 1506 to 1540 m/s (as indicated in Table 1) and acoustic attenuation lower than 0.1 Db/cm/MHz. Such polyacrylamide-in-water solid elastic thus provides an ideal matrix for the further development of ultrasound tissue-simulating and/or calibration materials.

TABLE 1

| % ACRYLAMIDE BY WEIGHT OF THE WATER CONTENT IN SAMPLE | 5 | 8 | 11 | 14 |
|---|---|---|---|---|
| SPEED OF SOUND METERS/SECONDS | 1506 | 1517 | 1528 | 1540 |

The compatibility of this matrix described above with other liquids allows the adjustment of the speed of sound in the ultrasonic material by using liquids which are miscible as well as non-miscible-to-water.

Figure 2:
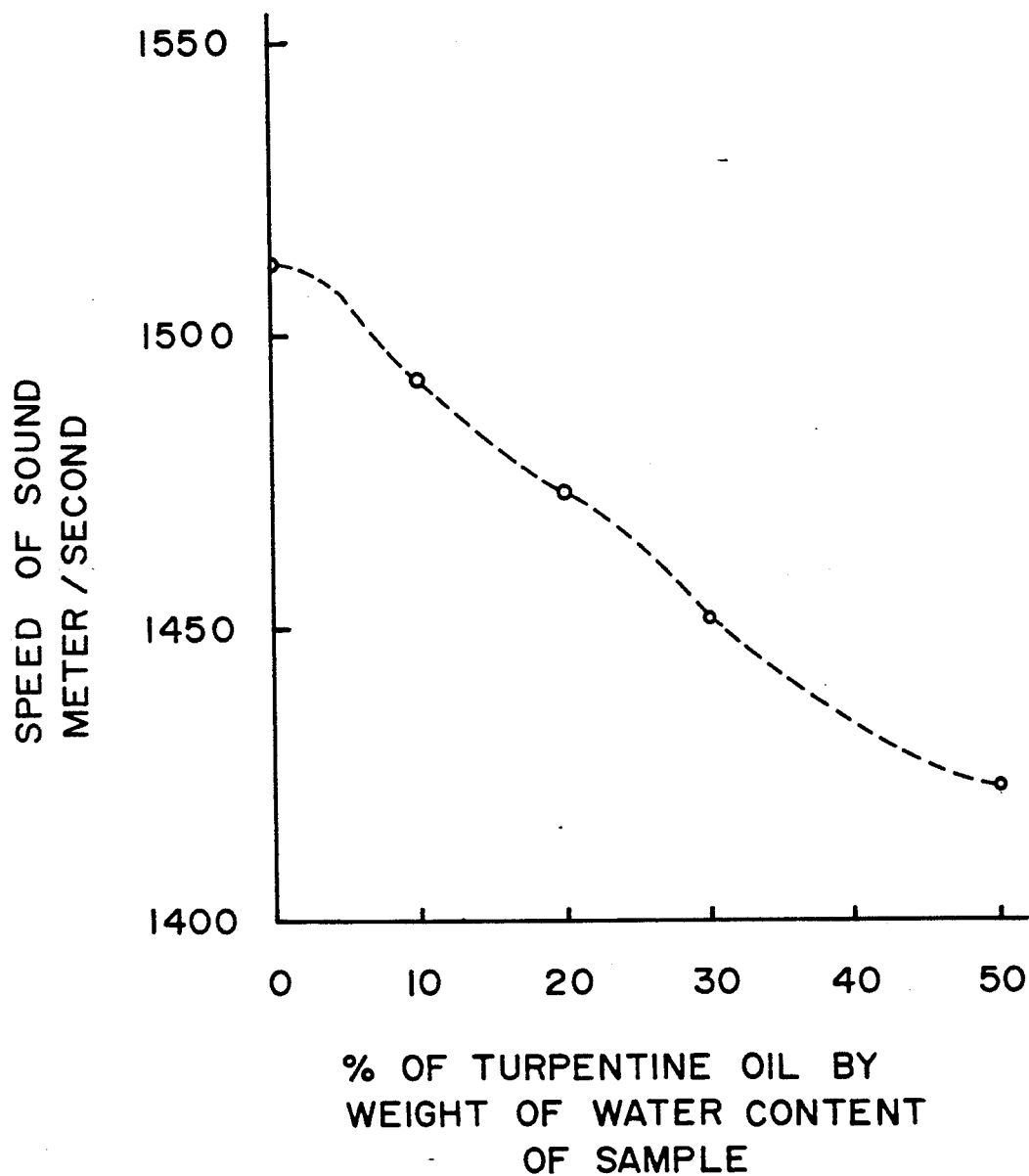
FIG. 2 is a chart showing speed of sound as a function of turpentine oil content in sample.

For the purpose of illustration but not of limitation, FIG. 1 demonstrates the ability to increase the acoustic speed as a function of the ethylene glycol content of the test material (1) and FIG. 2 demonstrates the ability to decrease the acoustic speed as a function of turpentine oil content of the test material (1).

The samples of test material (1) containing ethylene glycol displayed acoustic attenuation lower than 0.1 Db/cm/MHz up to 8 MHz allowing the adjustment of the acoustic attenuation with dampening particles beyond the range of attenuation exhibited by human tissues.

The samples with turpentine oil content of 20 to 30% by weight cover the range of speed displayed by fatty tissues and they exhibit acoustic attenuation of about 0.4 Db/cm/MHz also displayed by fatty tissues.

We observed that the acoustic attenuation can be further adjusted using additives in the matrix such as solid particles of alumina, boron nitride, graphite, glass microspheres, water-filled phenolic microspheres, and polyethylene micropowder.

When loaded with alumina, boron nitride, graphite or water-filled phenolic microspheres, we achieved proportionality of the acoustic attenuation with frequency as exhibited by human tissues.

When loaded with glass microspheres or polyethylene powder the acoustic attenuation increased exponentially as a function of the frequency as indicated in Table 2.

TABLE 2

| TYPICAL VALUES OF ATTENUATION FOR | FREQUENCY | | | | VALUES OF COEFFICIENT $A_O$ AND POWER COEFFICIENT n OF THE POWER REGRESSION ANALYSIS OF ATTENUATION AS A FUNCTION OF FREQUENCY |
|---|---|---|---|---|---|
| | 2.25 | 3.5 | 5 | 7.5 | |
| SAMPLE WITH 0.5% OF GLASS MICROSPHERES BY WEIGHT OF WATER IN SAMPLE | .64 | 1.77 | 4.59 | 6.1 | $A_O = .15$<br>$n = 1.94$<br>COEFFICIENT OF REGRESSION = .976 |
| SAMPLE WITH 5% OF POLYETHYLENE POWDER BY WEIGHT OF WATER IN SAMPLE | .62 | 1.75 | 3.65 | 5.75 | $A_O = .15$<br>$n = 1.86$<br>COEFFICIENT OF REGRESSION = .987 |

Figure 10:
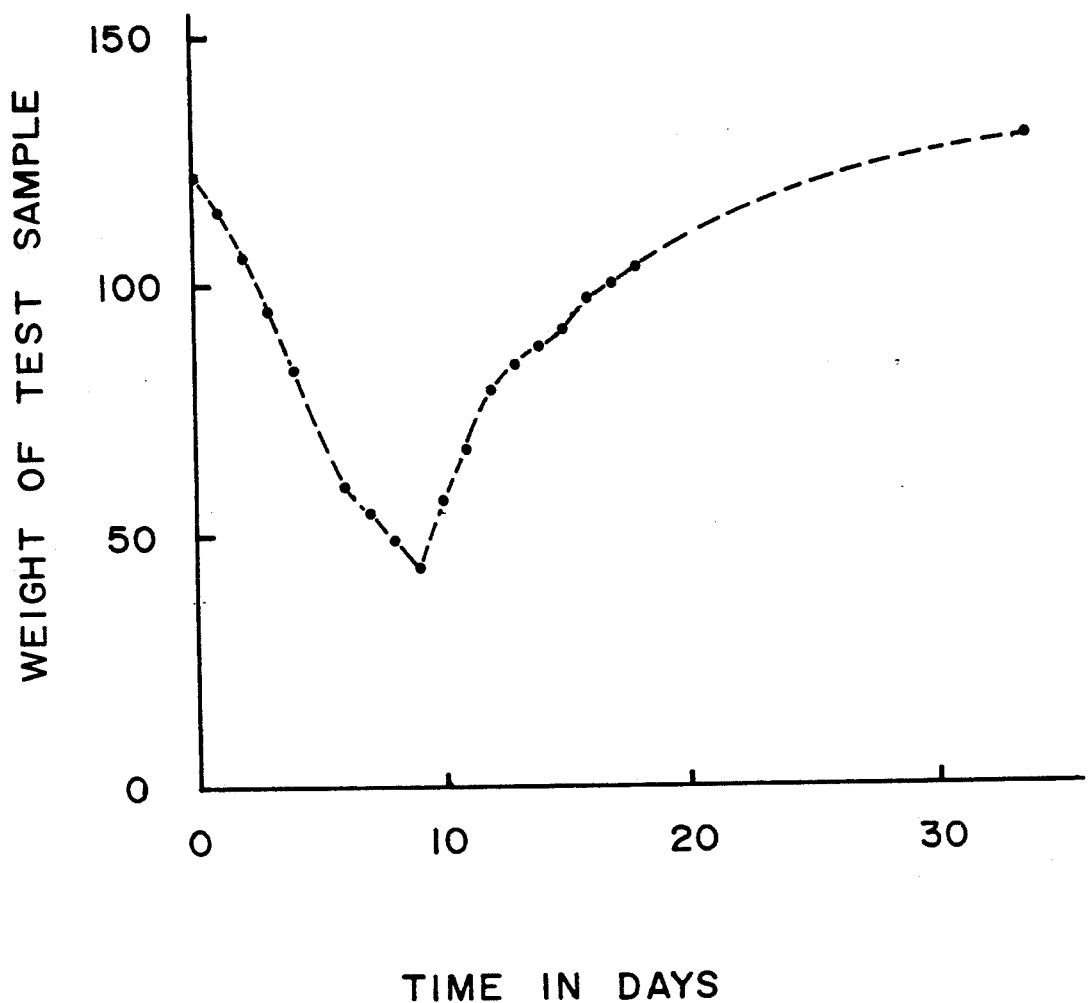
FIG. 10 is a chart showing the changes in the weight of a particular test sample when left unprotected in air and when immersed in water as a function of time.

We experienced that polyacrylamide water based ultrasound material reacts like a sponge and has the ability after desiccation to reabsorb the amount of lost water as demonstrated in FIG. 10. A sample of 122 grams of test material lost about 64% of its weight in a period of 8 days when left in air at room temperature. The same sample was then immersed in water at room temperature and regained its original weight and imaging properties after 20 days.

Water losses from desiccation of our ultrasound material due to leakage from its containing devices can be now easily compensated after immersion of the said material in a water bath. w This property, which is not shared by any other existing gel matrix, can be fully used in the design of an ultrasound test device in order to simplify its fabrication, to maintain the material in its original condition and to extend its useful life by preserving it from a major weakness which is leakage and desiccation.

A typical sample of this material having a cylindrical form of about 3.5 cm diameter and 3.5 cm height is capable of withstanding free fall of 5 meters without breakage or loss of imaging properties. This sample can then be sustained for five minutes in boiling water and the only change detected is an increase in weight of 1.3%. The sample regains its original weight when left in air for about 10 minutes.

The physical characteristics of our material, as illustrated in the paragraph above, permit the use and handling of the material with or without a protective envelope. Additionally, in certain applications, the ultrasonic instruments can be placed in direct contact with said ultrasonic calibration material, thus eliminating the sonic interference of a protective envelope.

An adequate ultrasonic material must have a perfect homogeneity throughout its volume. It is an object of the present invention to provide a method of preparation of this material which assures such homogeneity while eliminating any residual air bubbles in it.

In the case of solid particle additives, we have been able to achieve chemically and at room temperatures, a homogeneous and permanent suspension before polymerization of the resin matrix using the suspending properties of an acrylic acid polymer which is mixed to the water phase in the amount of 0.1 to 0.5% by weight. In the present invention the said suspending properties, which are due to the polymerization of the said acrylic acid, are triggered and occur instantaneously by chemical neutralization of the acrylic acid by an inorganic base. This neutralization is irreversible.

In the case of liquid particles which are non-miscible-to-water, we first obtained an emulsion of such a liquid in water using a surfactant in the amount of 0.1 to 1% by weight of the water phase. The emulsion is then permanently stabilized using the same said acrylic acid polymer as described above.

Because gas bubbles have a tremendous effect on the sonic properties of the test material, the absence of gas bubbles in the material is a requisite. We satisfied such a condition by a vacuuming our mixture before the final step of the polymerization of the resin matrix which is to activate the initiator. We experienced that after vacuuming (but only after) all the mixtures, we are able to achieve repetitive results from batch to batch of the manufactured test material.

While the above description contains many specificities, the reader should not construe these as limitations on the scope of the invention, but merely as exemplifications of the preferred embodiments thereof. For example, the end use calibration requirement may dictate that said ultrasonic calibration materials be provided with wide ranging shapes, sizes, and physical characteristics to assist in developing new ultrasonic equipments or new ultrasonic imaging applications. Accordingly, the reader is requested to determine the scope of the invention by the appended claims and their legal equivalents, and not by the examples which have been given.

OPERATION/USE OF INVENTION

Having described the basic concept of the invention, illustration will be now made by way of examples which are given by way of illustration, and not by way of limitation.

EXAMPLE 1

Figure 3:
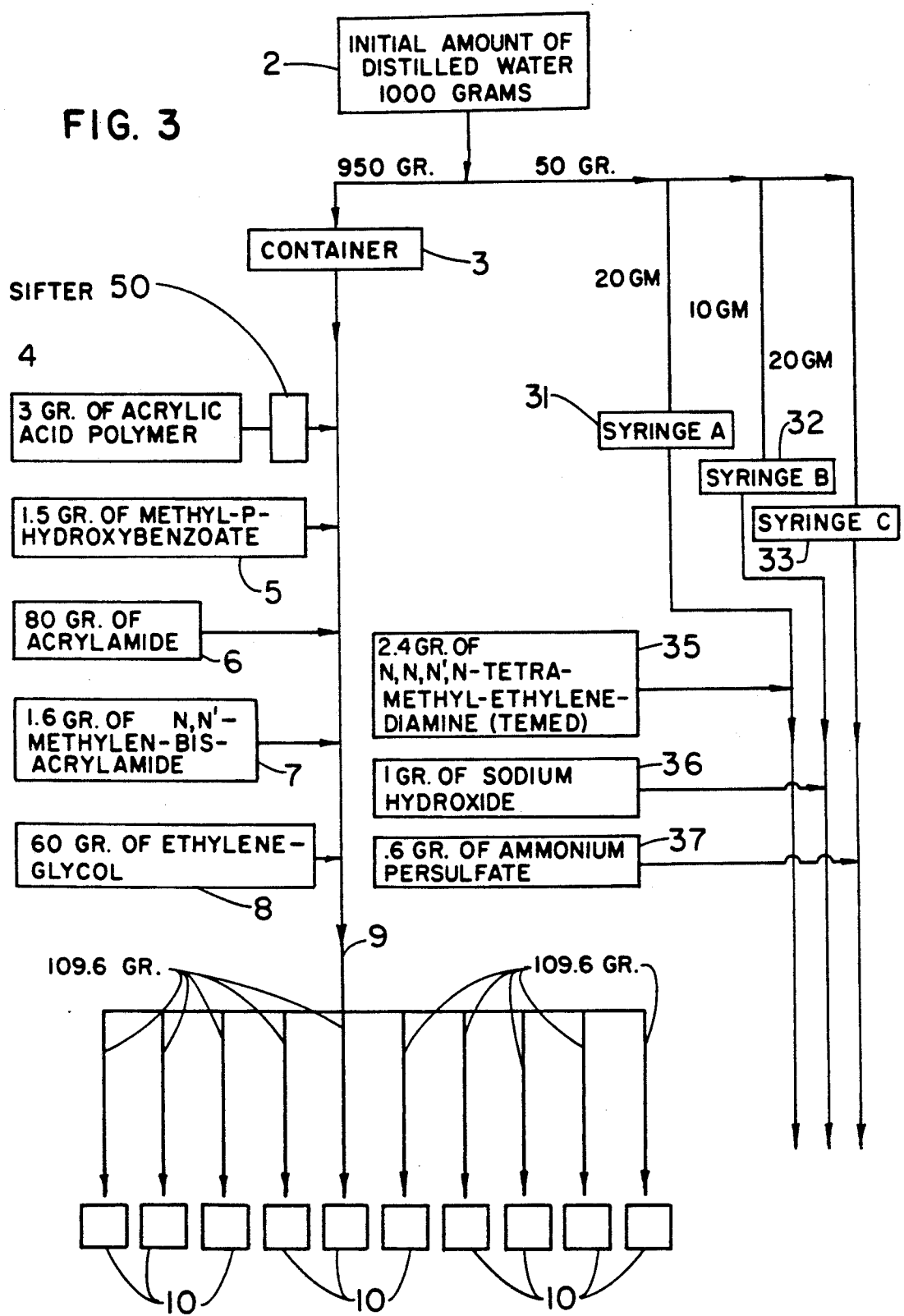
FIG. 3 is a flow-chart diagram showing the method of preparation and formulation of a base solution with an initial amount of 1000 grams of distilled water.
Figure 4:
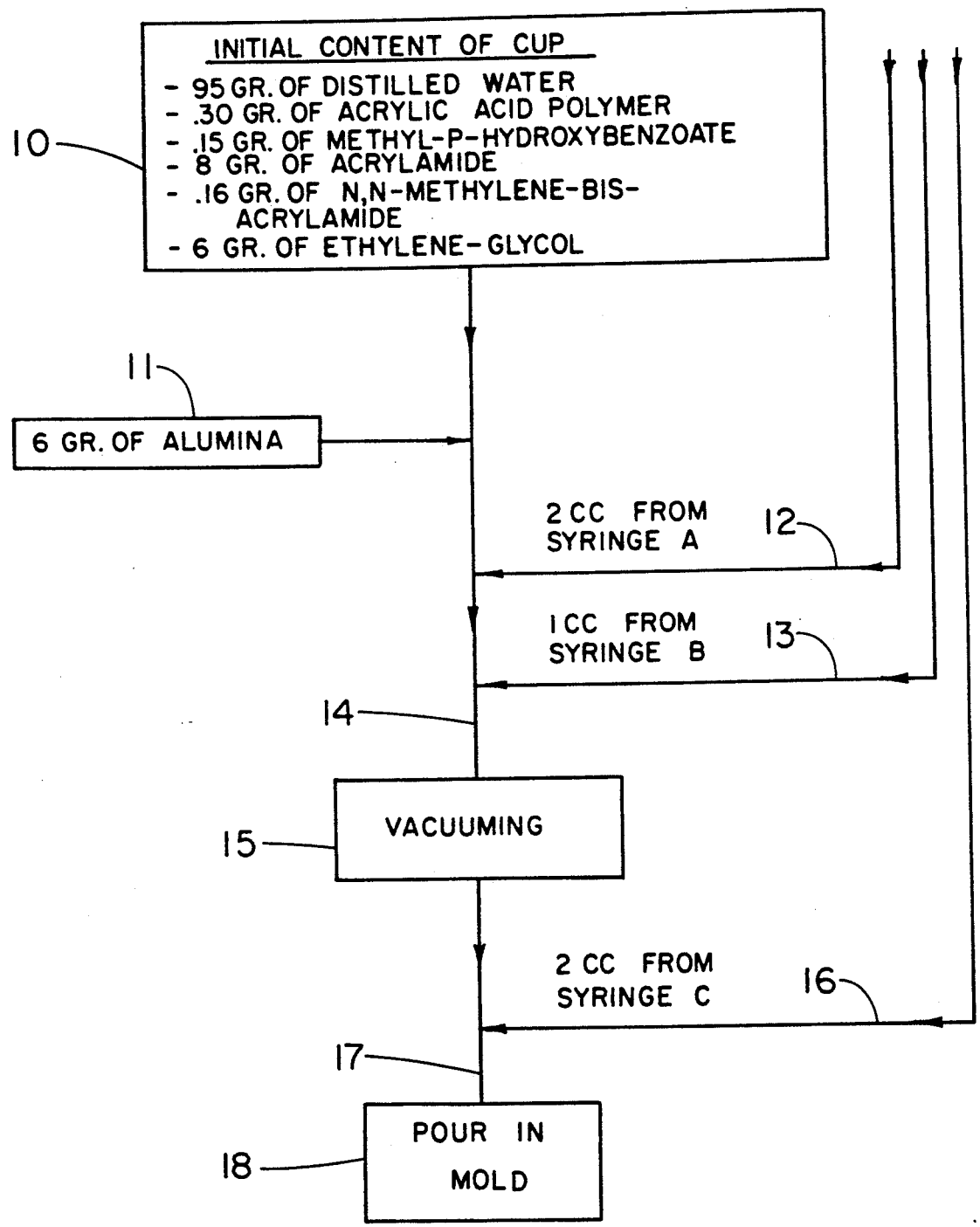
FIG. 4 is a flow-chart diagram showing the final steps of preparation of a particular test sample with 6% alumina by weight of the water in the sample.

Referring to FIG. 3 and FIG. 4: An initial amount of 1000 grams of distilled water (2) was used in the preparation of the samples. As outlined in FIG. 3, this amount was fractioned in a container (3) with 950 grams of water and in three 30 cc syringes (referenced syringe A, B, and C) with respectively 20, 10 and 20 grams of water.

An acrylic acid polymer (4) (produced by the Goodyear Company under the brandname of Carbopol) in the form of powder and in the amount of 0.3% by weight of the initial amount of water (i.e. 3 grams) was slowly added in the container (3) through a sifter (50) while mixing at room temperature until complete dissolution of the polymer. This step took about 10 minutes.

Methyl-p-benzoate (5) in the amount of 0.15% by weight of the initial amount of water (2) (i.e. 1.5 grams) was added in the container (3) while mixing at room temperature until complete dissolution. This step took about 2 minutes.

Acrylamide powder (6) in the amount of 8% by weight of the initial amount of water (2) (i.e. 80 grams) was added in the container (3) while mixing at room temperature until complete dissolution. This step took about 5 minutes.

N,N'-methylene-bis-acrylamide (7) (MBA) in the amount of 2% by weight of the previous weight of acrylamide powder (6) (i.e. 1.6 grams) was added in the container while mixing at room temperature until complete dissolution. This step took about 10 minutes.

Ethylene glycol (8) in the amount of 6% by weight of the initial amount of water (i.e. 60 grams) was added to the container and mixed for 1 minute at room temperature.

The solution (9) thus produced was then divided in ten equal parts in cups (10). The content of each cup (10) was then used in the production of a particular test sample (1).

In syringe A (31), containing 20 grams of water, an amount of 2.4 grams of N,N,N', N-tetra-methyl-ethylene-diamine (TEMED) (35) was diluted.

In syringe B (32), containing 10 grams of water, an amount of 1.0 grams of sodium hydroxide (36) was dissolved.

In syringe C (33), containing 20 grams of water, an amount of 0.6 grams of ammonium persulfate (AP) (37) was dissolved.

In this specific example, we used six cups (10) containing respectively 3, 6, 9, 12, 15 grams of alumina powder with an average particle size of one micron, and one cup with no additive in it.

As outlined in FIG. 4, a particular sample was prepared as follows:

The alumina powder (11) was added in the cup (10) containing the previously produced base solution and mixed for about one minute.

We then added to the cup (10), 2 cc of the solution (12) from syringe A (31) with TEMED while mixing at room temperature. The TEMED has a neutralizing effect on the acrylic acid polymer (4) which triggers the suspending properties of said acrylic acid polymer.

We added 1 cc of the solution (13) from syringe B (32) containing the sodium hydroxide while mixing at room temperature. By doing so, we completed the neutralization of the acrylic acid and we thus produced a solution (14) in which the alumina powder is now permanently suspended. We observed that the suspending process occurs instantaneously when either the TEMED solution or the sodium hydroxide solution is added.

The cup containing the solution (14) is then placed in a vacuum chamber (15). The vacuum is applied up to the point where the solution starts boiling. We maintained this level of vacuum for about 5 to 10 seconds and then released the vacuum completely. By so doing, we assured that the solution is perfectly degassed.

Finally, we added 2 cc from syringe C (33) containing the AP solution (16) while mixing the solution (17) in a blender (not shown) at very slow speed so that the AP is dispersed throughout the solution without entrapment of air bubbles.

Figure 5:
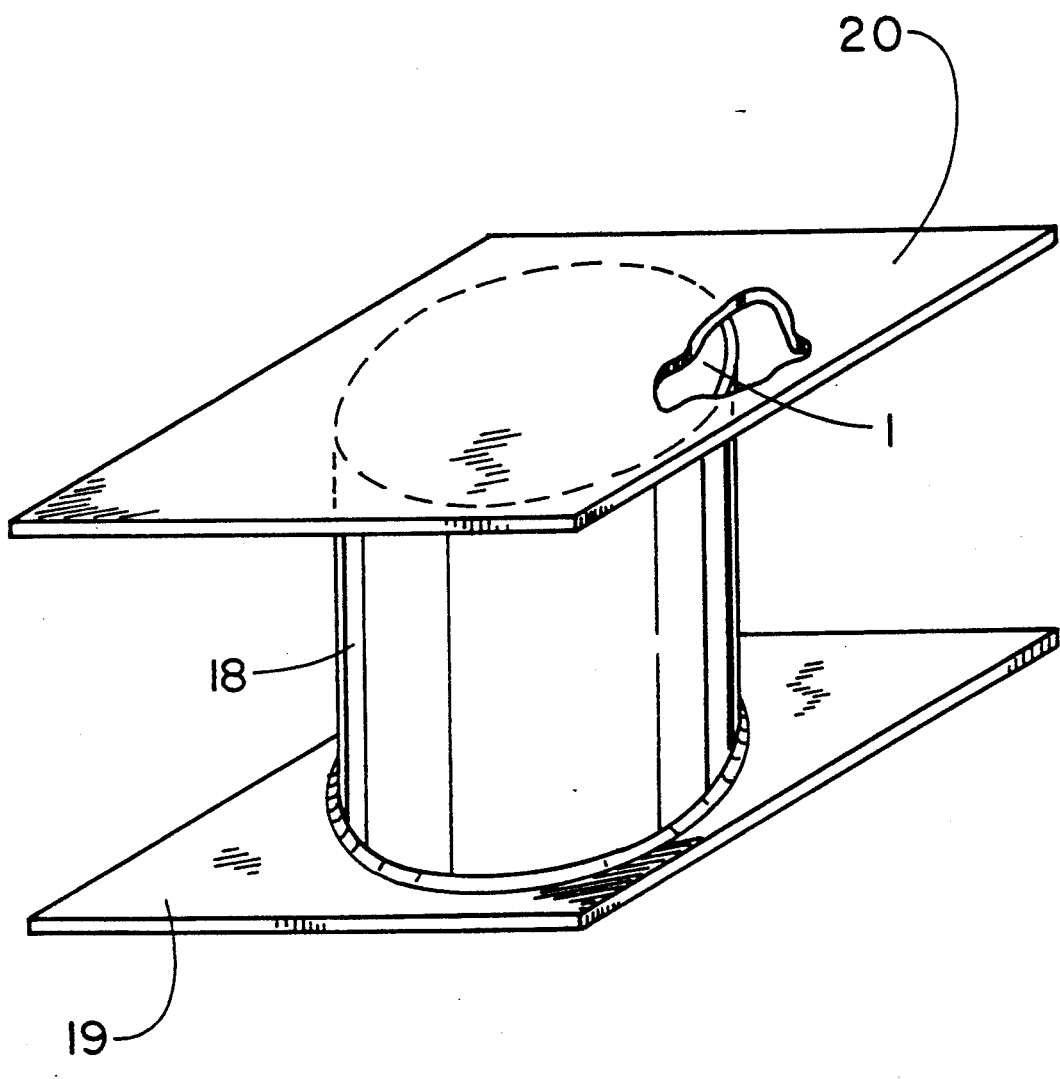
FIG. 5 is a perspective view showing a mold used to shape the test samples.

The solution (17) thus produced was then poured in a mold (18) having cylindrical shape with an inside diameter of 3.7 cm and a depth of 3.3 cm as illustrated in FIG. 5. The bottom (19) of the mold was made from perfectly flat glass. After the mold (18) has been filled up with solution (17), it was then covered with another piece of flat glass (20) in order to have full contact with the solution. By doing so, we assured having a sample with flat top and flat bottom scanning surfaces.

The polymerization of the resin matrix takes place quickly and is exothermic and we observed a slight increase in the sample temperature of about 10 degrees Celsius. The poured solution became a firm elastic after 5 to 10 minutes. The test sample (1) was left to cool in the mold until its temperature was equal to room temperature before demolding it.

Figure 6:
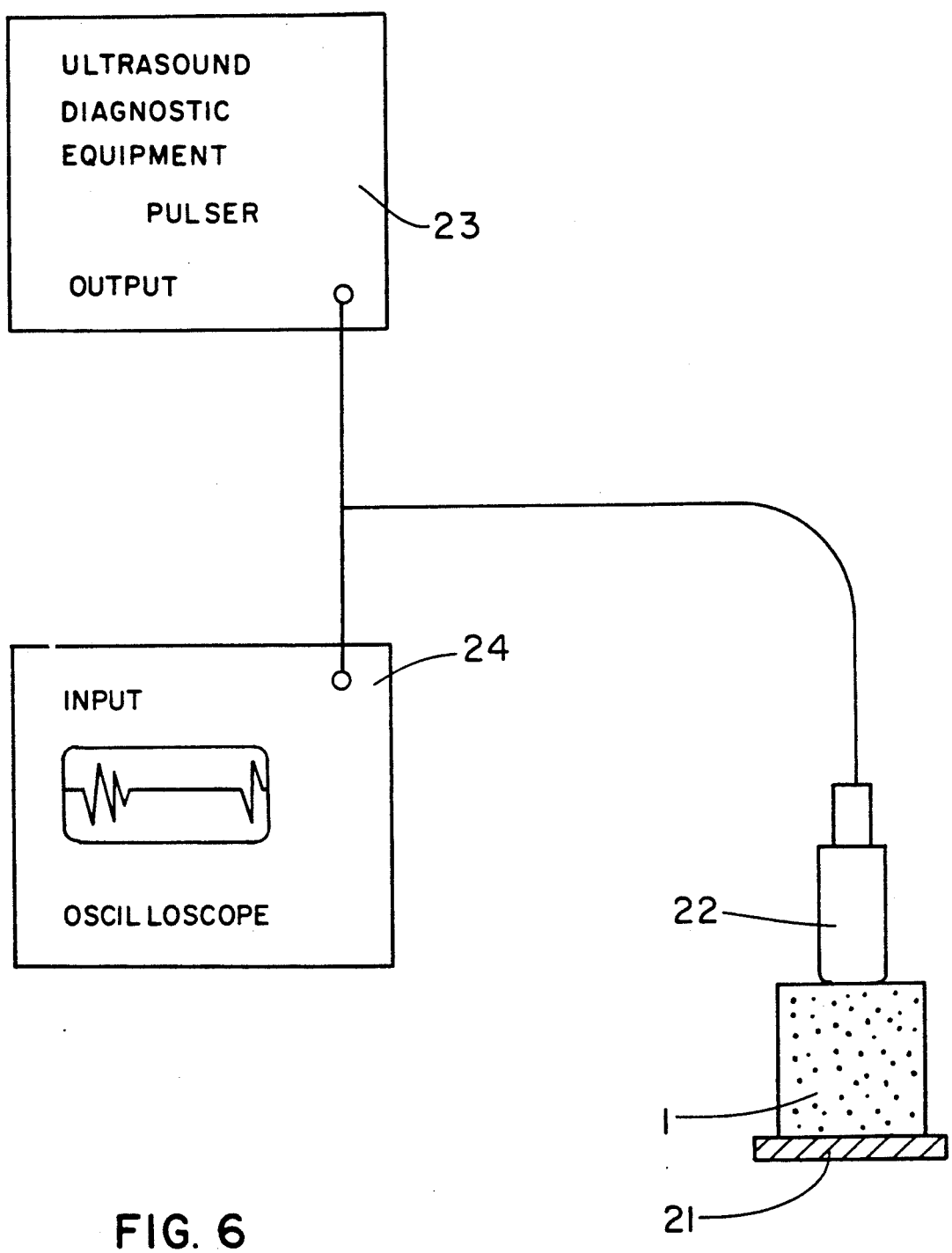
FIG. 6 is an schematic diagram of the apparatus used for evaluation of speed of sound and acoustic attenuation coefficients.

Evaluation of speed of sound and acoustic attenuations were made from measurements obtained with the apparatus shown in FIG. 6.

The samples (1) are self-standing and did not require to be supported. Measurements were taken while the sample (1) was placed on an ultrasonic reflective flat glass (21) with the single crystal transducer (22) directly in contact with the sample (1). (See FIG. 7).

As illustrated in FIG. 6, a narrow band pulser (23) was used to send ultrasound pulses through the test material (1) and which, after reflection on the glass (21), were received back by the transducer (22) and directed to a standard laboratory oscilloscope (24).

Figure 7:
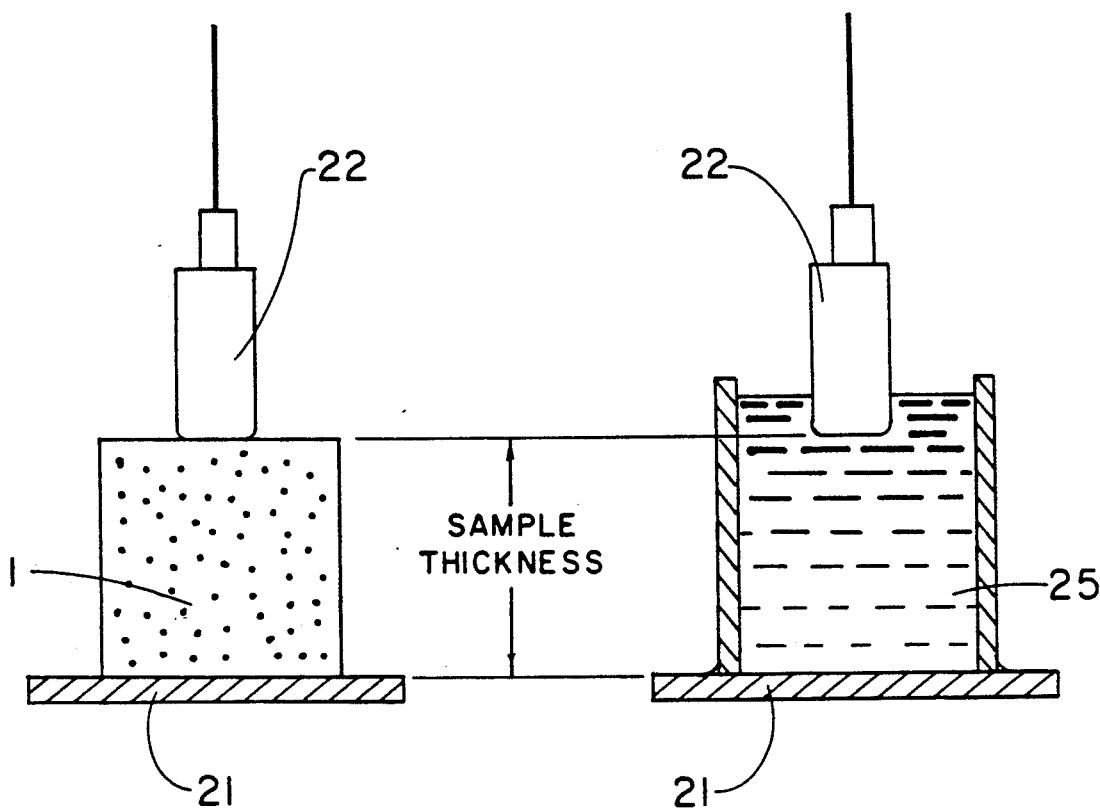
FIG. 7 is a schematic diagram of the present invention indicating the positioning of the ultrasound transducer with the sample and in water.

The speed of sound was evaluated by measuring the time difference of the received echo between the case A (where the sample (1) was between the transducer (22) and the reflective glass (21)) and case B (where the sample (1) was replaced by water (25)) as illustrated by case A and case B in FIG. 7. The speed is then calculated in relation to the speed of sound in water at room temperature which is acknowledged to be 1485 m/s.

Acoustic attenuations were evaluated using the same apparatus with transducers (22) producing sonic pulses of different ultrasonic frequencies by measuring the amplitude of the sonic echo in both cases A and B, respectively as described above.

Figure 8:
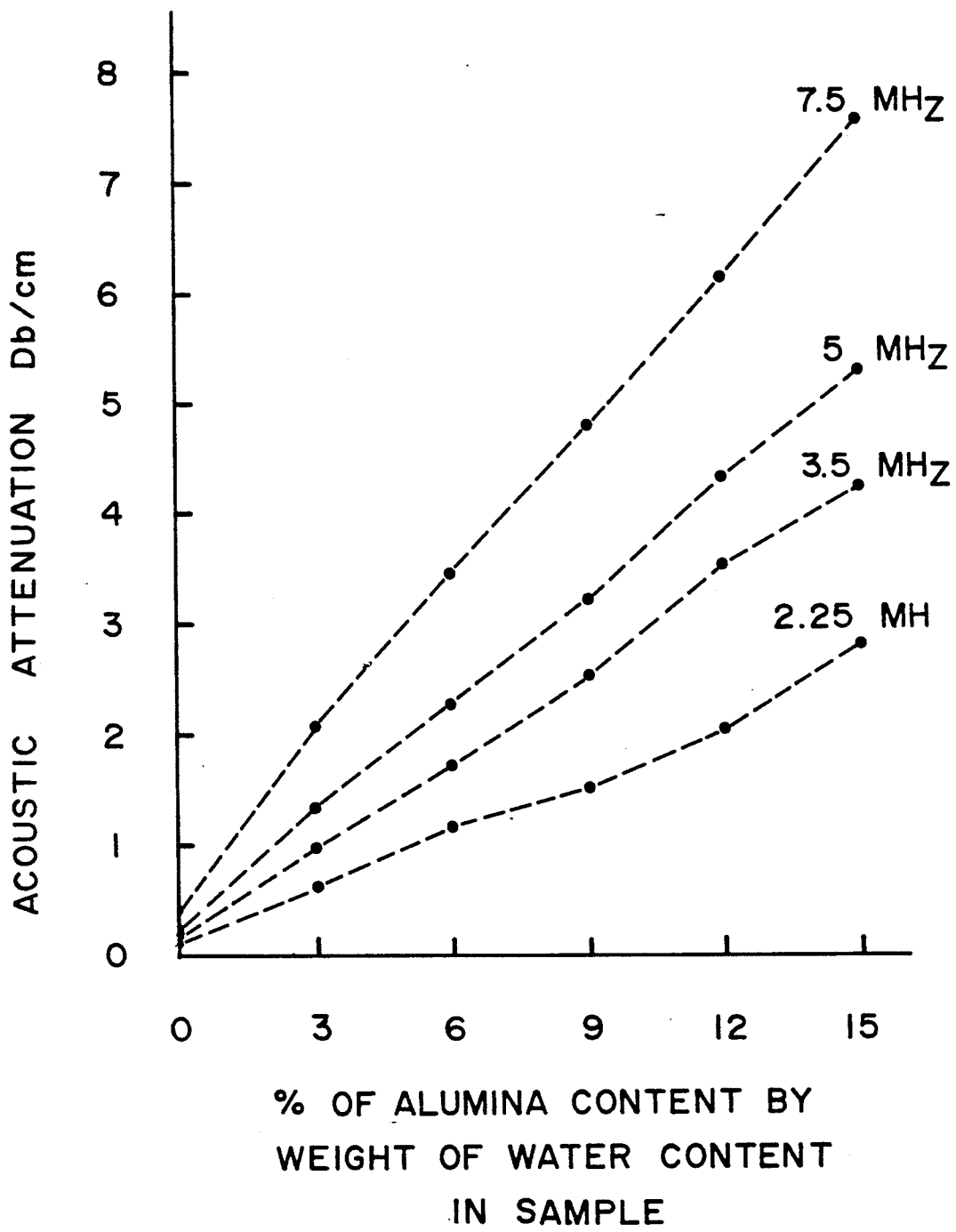
FIG. 8 is a chart showing acoustic attenuation coefficients as a function of the alumina content in the test samples for different ultrasonic frequencies.
Figure 9:
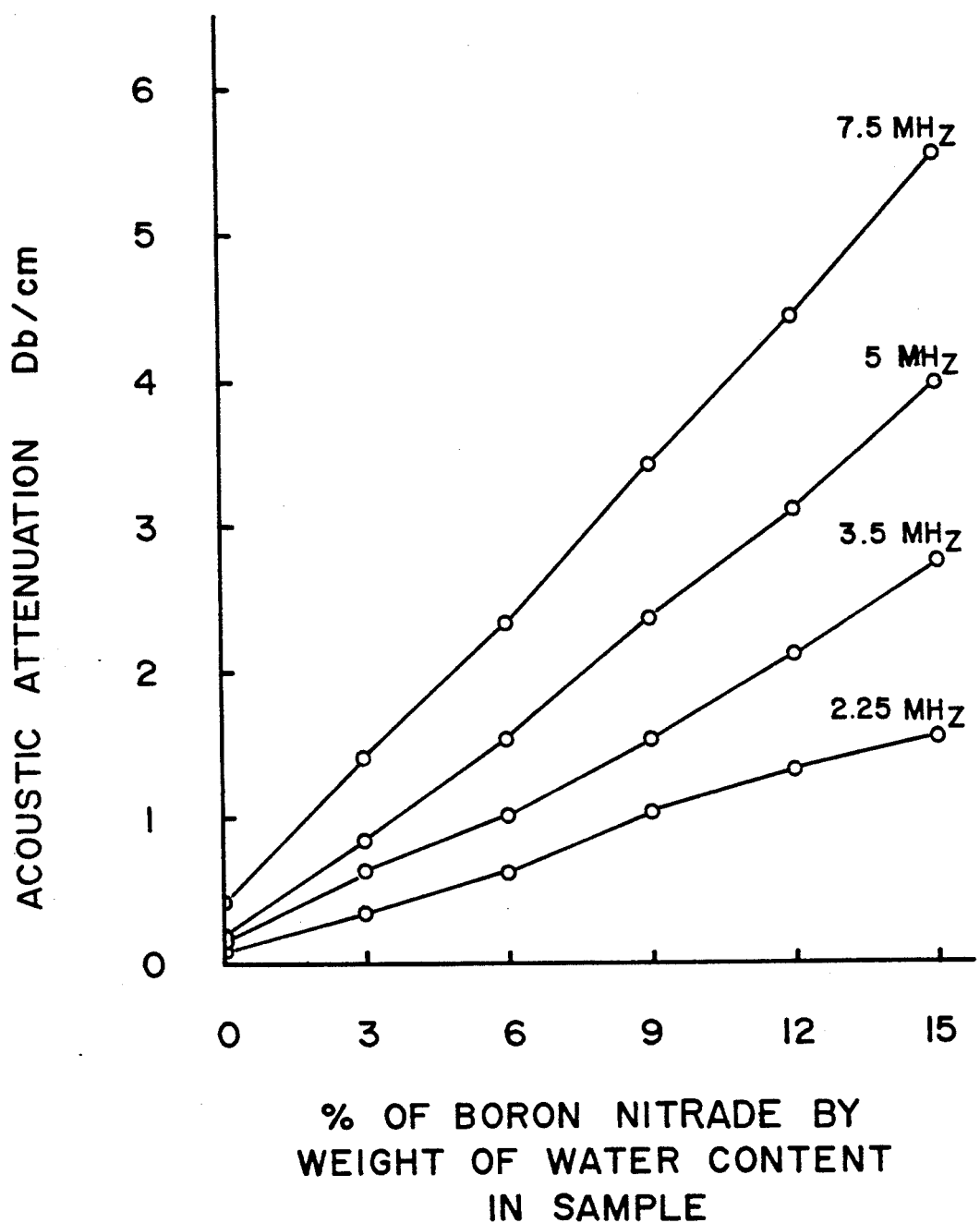
FIG. 9 is a chart showing acoustic attenuation coefficients as a function of the boron nitride content of the test sample for different ultrasonic frequencies.

The results, as shown in FIG. 8, demonstrate the ability to adjust the attenuation from 0.1 up to 1.5 Db/cm/MHz by adjusting the amount of alumina powder up to 20% by weight of the amount of water in the sample.

The speed of sound decreases slightly from 1530 m/s down to 1505 m/s for the sample we evaluated as indicated in Table 3.

TABLE 3

| % OF ALUMINA BY WEIGHT OF THE CONTENT WATER IN SAMPLE | CALCULATED VALUES OF SPEED OF SOUND IN SAMPLE METERS/SECONDS | REGRESSION ANALYSIS ASSUMING A RELATION OF THE FORM $A = A_0 f^n$ BETWEEN THE ACOUSTIC ATTENUATION A AND FREQUENCY f | | |
|---|---|---|---|---|
| | | $A_0$ | n | COEFFICIENT OF CORRELATION |
| 0 | 1530 | .05 | .933 | .9044 |
| 3 | 1526 | .268 | 1.015 | .9988 |
| 6 | 1516 | .538 | .917 | .9989 |

TABLE 3-continued

| % OF ALUMINA BY WEIGHT OF THE CONTENT WATER IN SAMPLE | CALCULATED VALUES OF SPEED OF SOUND IN SAMPLE METERS/SECONDS | REGRESSION ANALYSIS ASSUMING A RELATION OF THE FORM $A = A_0 f^n$ BETWEEN THE ACOUSTIC ATTENUATION A AND FREQUENCY f | | |
|---|---|---|---|---|
| | | $A_O$ | n | COEFFICIENT OF CORRELATION |
| 9 | 1512 | .735 | .931 | .9961 |
| 12 | 1509 | 1.14 | .84 | .9931 |
| 15 | 1505 | 1.475 | .81 | .9995 |

As shown in Table 3, the values of the power coefficient n from regression analysis, demonstrate that the coefficient is approximately proportional to the frequency. The values of the coefficient $A_0$ which indicate the theoretic value of the attenuation for a frequency of 1 MHz covers the range of 0.05 to 1.5 Db/cm/MHZ.

EXAMPLE 2

The same procedures as described in example 1 were followed to produce samples containing different amounts of boron nitride powder with an average particle size of 10 microns.

Using the same apparatus and method as described in example 1, speed of sound and attenuations were evaluated for samples with respectively 3, 6, 9, 12, and 15% boron nitride powder by weight of the water amount in the sample.

The speed of sound in those samples appeared to be the same for all the samples and at the level of 1535 m/s as indicated in Table 4.

As indicated from the values of the coefficients $A_0$, the range of acoustic attenuation covered by the samples is from 0.15 up to 0.70 Db/cm/MHz which we do not in any case consider as an upper limit for materials using boron nitride. n The required amount of turpentine oil (26) was added to the cup containing the base solution. While mixing, 0.5% of surfactant (34) by weight of the water content of the sample was added in the cup (10a) (the surfactant is produced by the Dupont Company under the brandname Dupanol G). The speed of mixing was increased and maintained for 2 minutes in order to produce an emulsion of turpentine oil in water.

From the syringe (12) containing the solution of TEMED we added 2 cc in the cup then we added 1 cc from the syringe (13) containing the sodium hydroxide solution while mixing. Through this procedure, we achieved a permanently stabilized emulsion (14a).

Figure 14:
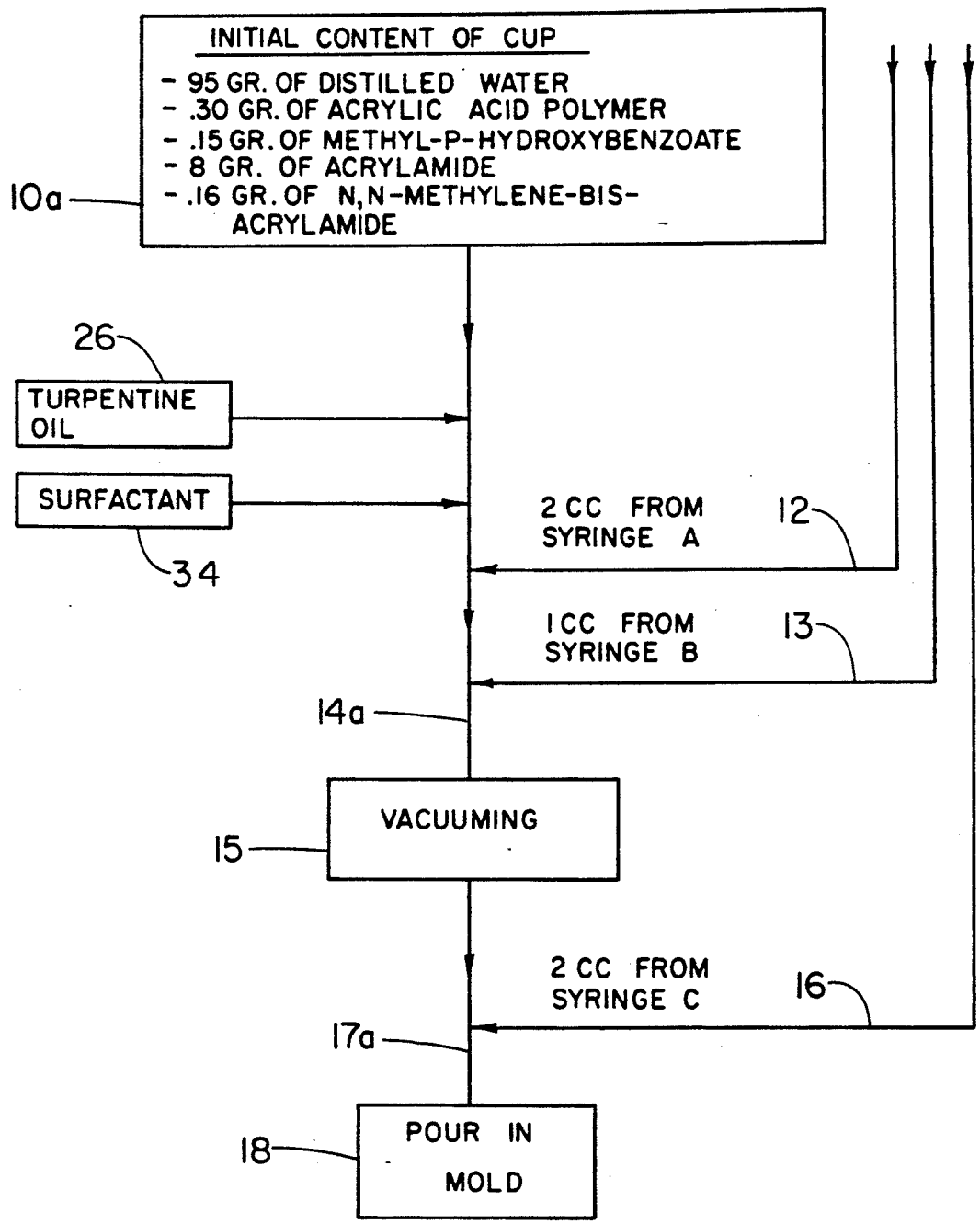
FIG. 14 is a flow chart diagram showing the final steps of preparation of a particular sample containing turpentine oil.

The same steps as described in example 1 were then followed to complete the production of the sample (See FIG. 14).

As shown in FIG. 2, the measurements made with thus produced samples show a linear relationship between the speed of sound and the turpentine content of the sample and demonstrate the ability to decrease the speed of sound to about 1420 m/s.

EXAMPLE 4

Figure 11:
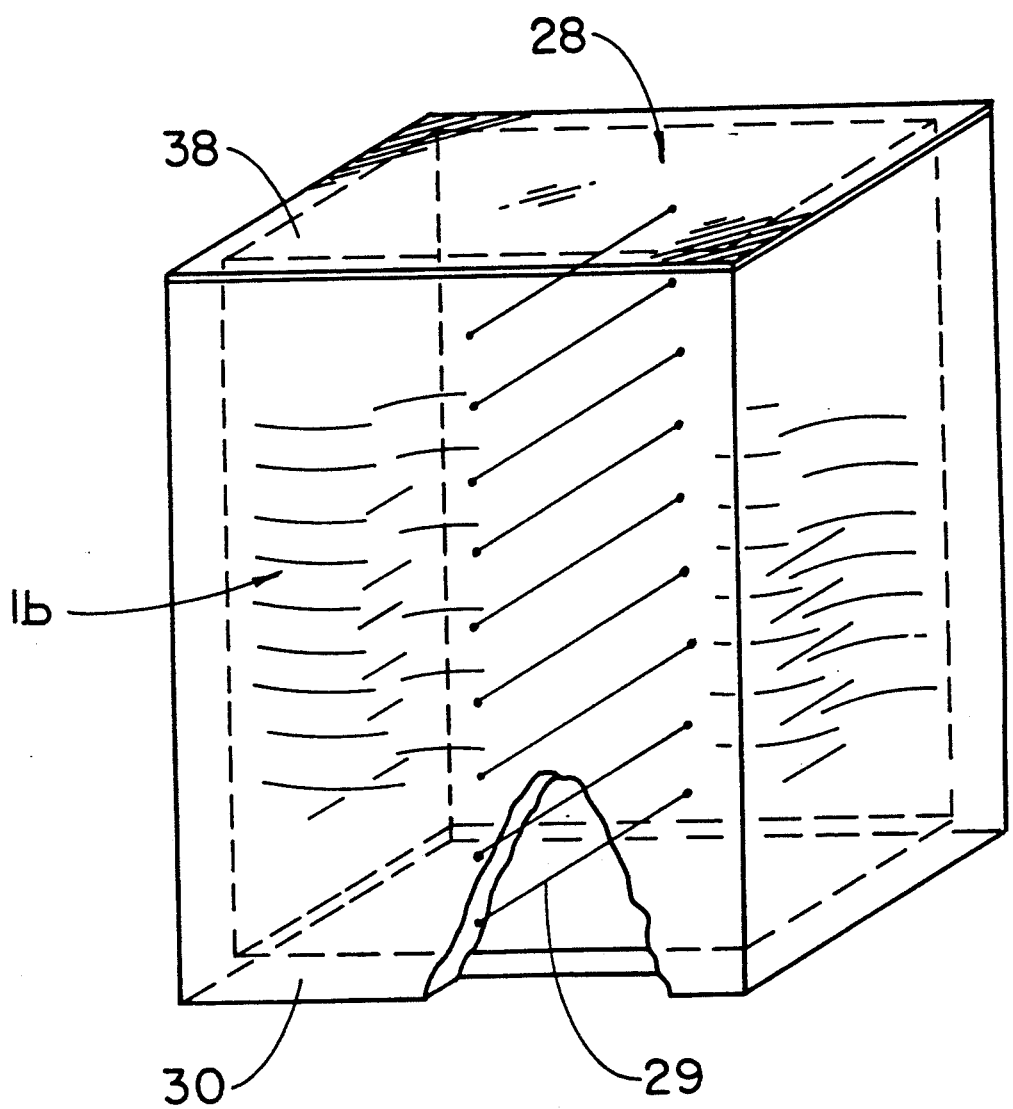
FIG. 11 is a perspective view showing a particular test sample of parallelepiped shape encased by a poly(methyl)methacrylate (PMMA) tank.
Figure 12:
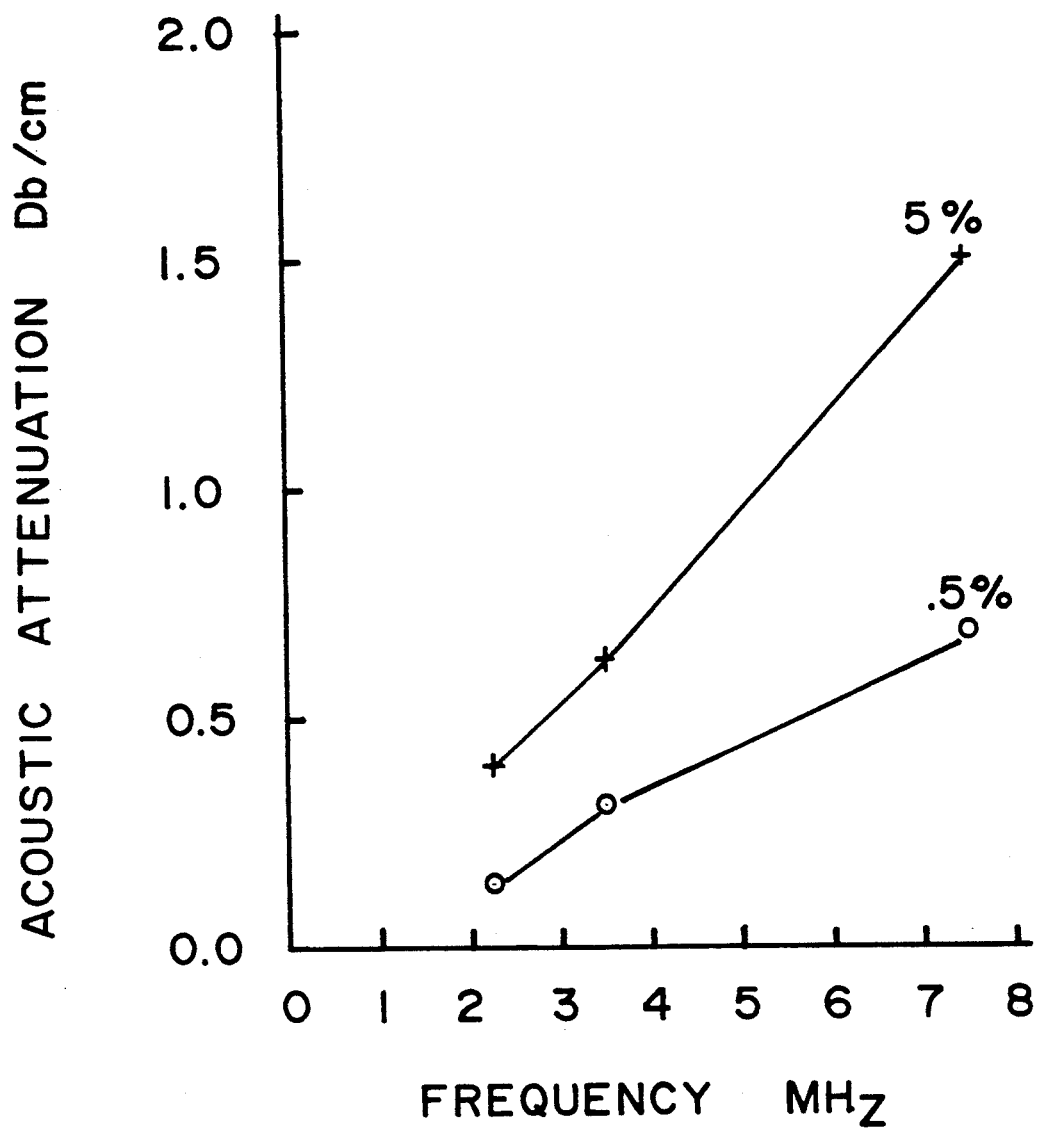
FIG. 12 is chart showing acoustic attenuation as a function of frequency for two (2) test samples containing water filled phenolic microspheres.

Referring to FIG. 11, the procedural steps as reported for example 1, were followed to create a sample

TABLE 4

| % OF BORON NITRIDE BY WEIGHT OF THE CONTENT WATER IN SAMPLE | CALCULATED VALUES OF SPEED OF SOUND IN SAMPLE METERS/SECONDS | REGRESSION ANALYSIS ASSUMING A RELATION OF THE FORM $A = A_0 f^n$ BETWEEN THE ACOUSTIC ATTENUATION A AND FREQUENCY f | | |
|---|---|---|---|---|
| | | $A_O$ | n | COEFFICIENT OF CORRELATION |
| 3 | 1535 | .153 | 1.110 | .9983 |
| 6 | 1533 | .264 | 1.092 | .9992 |
| 9 | 1535 | .423 | 1.015 | .9989 |
| 12 | 1533 | .594 | 1.013 | .9989 |
| 15 | 1533 | .677 | 1.073 | .9946 |

The values of the power coefficient n, as shown in Table 4, demonstrate a very good proportionality of the acoustic attenuation with the frequency and also demonstrate more stable values for the power coefficient n than samples loaded with alumina powder.

EXAMPLE 3

Figure 13:
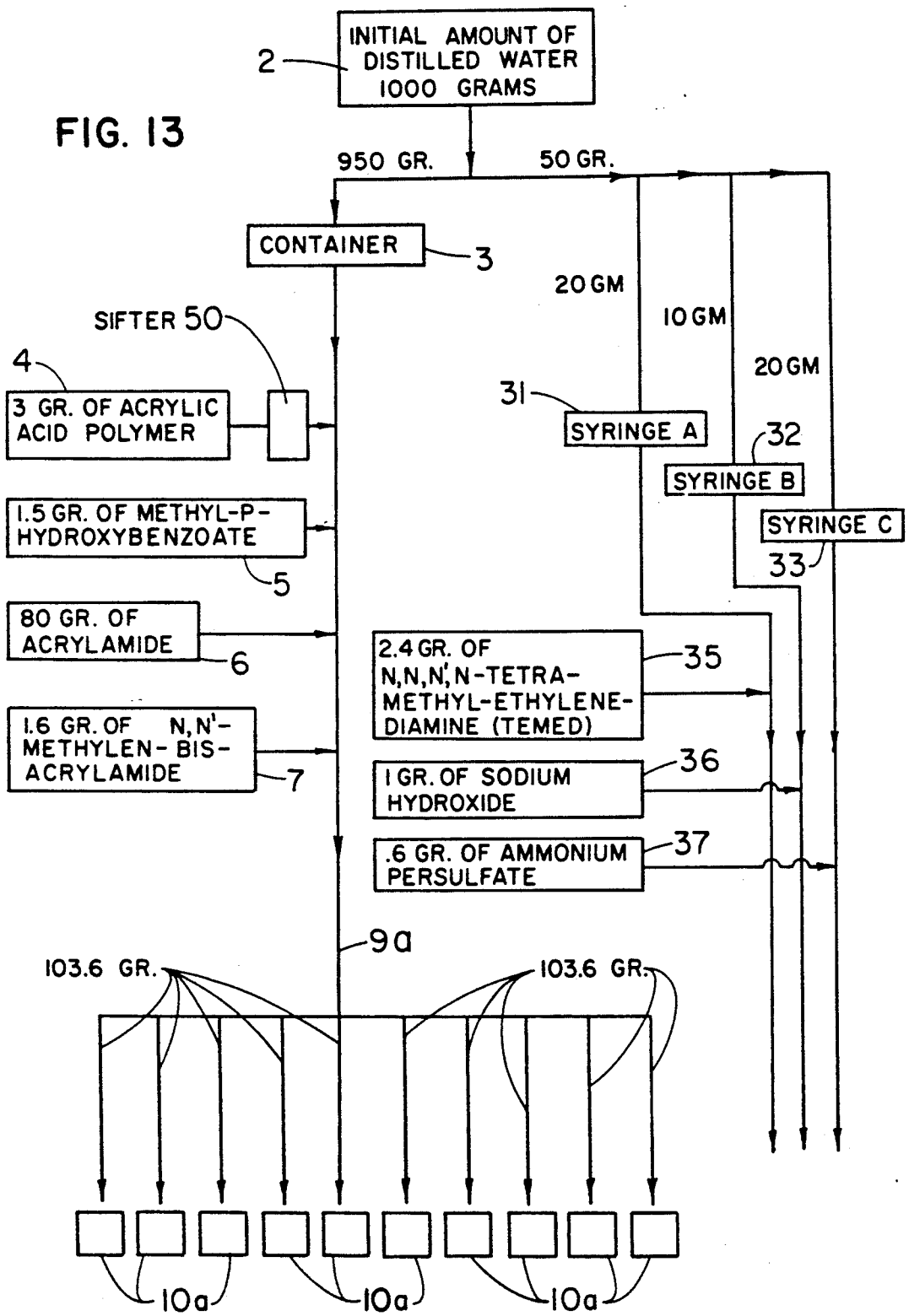
FIG. 13 is a flow chart diagram showing the method of preparation and formulation of a base solution without ethylene glycol for an initial amount of 1000 grams of water.

Referring to FIGS. 13 and 14: Following the same procedures as indicated in example 1, three syringes with respectively a solution containing TEMED, a solution containing AP, and a solution containing sodium hydroxide were prepared as well as a container with the base solution except that ethylene glycol was not added to this base solution (9a).

The solutions described above were used to prepare samples containing respectively 5, 10, 20, 30, and 50% of turpentine oil by weight of the water content of the sample.

Such samples were prepared as follows:

(1b) containing 6.3% alumina powder of 1 micron size and 6% ethylene glycol by weight of the water content of the sample. The sample (1b) was shaded as a rectangular parallelepiped having a 19 cm depth and a top (28) of 8 cm width, 15 cm long. Echogenic artifacts such as nylon monofilaments (29) were embedded in the sample (1b) along its width at different depths as shown in FIG. 11.

The sample (1b) was encased in a poly(methyl)methacrylate (PMMA) tank (30) having inside geometric dimensions identical to the sample dimensions except that the top of the tank was left open. The top side of the parallelepiped sample in the tank (30) was then covered by a thin membrane (38) of 30 micron thickness.

Scanning of the sample (1b) through the membrane (38) located on the top surface (28) of the sample was conducted with medical ultrasound imagers (not shown).

The assessment made from the images thus obtained from the sample demonstrated a gray scale echo appearance identical to the human liver. The speed of sound in the sample was evaluated by such equipment to be about 1540 m/s which is the speed assumed by medical ultrasound imaging equipments.

It will be understood that changes may be made in the details of formulation and operation without departing from the spirit of the invention especially as defined in the following claims:

We claim:

1. An ultrasonic calibration material comprising, a solid elastic material;
   said solid elastic material comprising a vacuum degassed, liquid based acrylamide polymerized resin matrix;
   wherein, said liquid comprises ethylene glycol and, wherein, said resin matrix comprises homogeneously suspended particles and a suspending agent.

2. An ultrasonic calibration material comprising, a solid elastic material,
   said solid elastic material comprising a vacuum degassed, liquid based acrylamide polymerized resin matrix,
   wherein, said liquid comprises ethylene glycol and, wherein, said resin matrix comprises homogeneously suspended particles and a suspending agent,
   wherein said solid elastic material has a speed of sound within the range of 1420 m/s to 1650 m/s, and,
   said solid elastic material has a sonic attenuation within the range of 0.1 to 1.5 Db/cm/MHz in the frequency range of 2 to 10 MHz; and,
   said solid elastic material has backscatter reflection characteristics within the range of backscatter of living tissue.

3. An ultrasonic calibration material comprising:
   a solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein said liquid comprises ethylene glycol, and,
   said resin matrix comprising homogeneously suspended particles and a suspending agent.

4. An ultrasonic calibration material comprising:
   a solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein such liquid comprises an emulsion of ethylene glycol, water, and nonmiscible-to-water liquids formed by the use of a surfactant, and,
   said resin matrix comprising homogeneously suspended particles and a suspending agent.

5. An ultrasonic calibration material comprising:
   a solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein such liquid comprises ethylene glycol, water and miscible-to-water liquids, and,
   said resin matrix comprising homogeneously suspended particles and a suspending agent.

6. An ultrasonic calibration material comprising:
   a solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein such liquid comprises ethylene glycol, water, and non miscible-to-water liquids formed by the use of a surfactant, and said non miscible-to-water liquids comprise turpentine oil, and,
   said resin matrix comprising homogeneously suspended particles and suspending agent.

7. An ultrasonic calibration material comprising:
   solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein said liquid comprises ethylene glycol, and,
   said resin matrix comprising homogeneously suspended particles and a suspending agent;
   wherein said suspended particles comprise alumina powder, boron nitride powder, graphite powder, water-filled phenolic microspheres, glass microspheres, or polyethylene powder.

8. An ultrasonic calibration material comprising:
   a solid elastic material,
   said solid elastic material having a calibrated speed of sound, sonic attenuation and backscatter reflection characteristics, each of said calibrated speed of sound, said sonic attenuation and said backscatter reflection characteristics being definable within the range of speed, attenuation and backscatter, respectively, of living tissue;
   said solid elastic material comprising a vacuum degassed, liquid based acrylamide polymerized resin matrix, wherein said liquid comprises ethylene glycol, and,
   said resin matrix comprising homogeneously suspended particles and a suspending agent;
   wherein the suspending agent is a chemically neutralized acrylic acid polymer.

9. Ultrasonic calibration material as claimed in 8 in which the neutralization is achieved by a solution of sodium hydroxide in water. a

* * * * *